(12) United States Patent
Dail et al.

(10) Patent No.: US 10,690,806 B2
(45) Date of Patent: Jun. 23, 2020

(54) WEATHER FORECASTS THROUGH POST-PROCESSING

(71) Applicant: THE CLIMATE CORPORATION, San Francisco, CA (US)

(72) Inventors: Holly Dail, Seattle, WA (US); Stephan Hoyer, San Francisco, CA (US)

(73) Assignee: The Climate Corporation, San Francisco, CA (US)

( * ) Notice: Subject to any disclaimer, the term of this patent is extended or adjusted under 35 U.S.C. 154(b) by 1120 days.

(21) Appl. No.: 14/681,886

(22) Filed: Apr. 8, 2015

(65) Prior Publication Data
US 2016/0299255 A1    Oct. 13, 2016

(51) Int. Cl.
| | | |
|---|---|---|
| *G01V 99/00* | (2009.01) | |
| *G01N 21/359* | (2014.01) | |
| *G01N 33/00* | (2006.01) | |
| *G06Q 10/04* | (2012.01) | |
| *G01W 1/10* | (2006.01) | |

(Continued)

(52) U.S. Cl.
CPC ......... *G01V 99/005* (2013.01); *G01N 21/359* (2013.01); *G01N 33/0098* (2013.01); *G01N 33/24* (2013.01); *G01W 1/10* (2013.01); *G06Q 10/04* (2013.01); *A01B 79/005* (2013.01); *G01N 2021/1793* (2013.01);
(Continued)

(58) Field of Classification Search
CPC ............................... G01W 1/10; G06Q 10/04
USPC ............................................................ 702/3
See application file for complete search history.

(56) References Cited

U.S. PATENT DOCUMENTS

| | | |
|---|---|---|
| 5,668,719 A | 9/1997 | Bobrov et al. |
| 5,796,932 A | 8/1998 | Fox |

(Continued)

FOREIGN PATENT DOCUMENTS

| | | |
|---|---|---|
| EP | 2196085 A2 | 6/2010 |
| EP | 2 244 108 A2 | 10/2010 |

(Continued)

OTHER PUBLICATIONS

European Patent Office, "Search Report", in application No. PCT/US2015/049456, dated Nov. 9, 2015, 13 pages.

(Continued)

*Primary Examiner* — Anthony Ho
(74) *Attorney, Agent, or Firm* — Elliot H. Karlin; Hickman Palermo Becker Bingham LLP

(57) ABSTRACT

A method for calibrating forecasts involving temperature, precipitation, and other weather related variables is provided. In an embodiment historical ensemble-based forecasts and historical observations are received by an agricultural intelligence computing system. Historical differences are determined between the forecasts and the observations corresponding to the forecasts and stored in the volatile memory of the agricultural intelligence computing system. The agricultural intelligence computing system receives current ensemble-based forecasts and a request for improved forecasts. The agricultural intelligence computing system retrieves the historical differences and uses a combination of the historical differences and the current ensemble-based forecasts to create probability distributions for the weather for each lead day. The agricultural intelligence computing system then samples from the probability distributions to create improved ensemble-based forecasts at the requested location.

19 Claims, 6 Drawing Sheets

(51) Int. Cl.
- *G01N 33/24* (2006.01)
- *G01N 21/17* (2006.01)
- *G01N 21/31* (2006.01)
- *A01B 79/00* (2006.01)

(52) U.S. Cl.
CPC ............... *G01N 2021/3155* (2013.01); *G01N 2201/0616* (2013.01); *G01N 2201/129* (2013.01)

(56) References Cited

U.S. PATENT DOCUMENTS

| | | |
|---|---|---|
| 6,535,817 B1 | 3/2003 | Krishnamurti |
| 9,076,118 B1 | 7/2015 | Mewes |
| 2002/0133505 A1 | 9/2002 | Kuji |
| 2002/0183867 A1 | 12/2002 | Gupta |
| 2004/0064255 A1 | 4/2004 | Egi |
| 2006/0004907 A1 | 1/2006 | Pape |
| 2006/0167926 A1 | 7/2006 | Verhey et al. |
| 2007/0085673 A1 | 4/2007 | Krumm |
| 2008/0287662 A1 | 11/2008 | Wiesman |
| 2012/0083907 A1 | 4/2012 | Motavalli et al. |
| 2013/0173321 A1 | 7/2013 | Johnson |
| 2013/0174040 A1 | 7/2013 | Johnson |
| 2013/0332205 A1 | 12/2013 | Friedberg et al. |
| 2014/0012732 A1 | 1/2014 | Lindores |
| 2014/0067745 A1 | 3/2014 | Avey et al. |
| 2014/0089045 A1 | 3/2014 | Johnson |
| 2015/0370935 A1 | 12/2015 | Starr |
| 2016/0078375 A1 | 3/2016 | Ethington et al. |
| 2016/0078569 A1 | 3/2016 | Ethington et al. |
| 2016/0078570 A1 | 3/2016 | Ethington et al. |

FOREIGN PATENT DOCUMENTS

| | | |
|---|---|---|
| WO | WO 2009/048341 A1 | 4/2009 |
| WO | WO2010128864 A1 | 11/2010 |
| WO | WO 2011/064445 A1 | 6/2011 |
| WO | WO 2014/036281 A2 | 3/2014 |

OTHER PUBLICATIONS

European Patent Office, "Search Report" in application No. PCT/US2015/049466, dated Nov. 9, 2015, 12 pages.
European Patent Office, "Search Report" in application No. PCT/US2015/049464, dated Nov. 9, 2015, 11 pages.
European Claims in application No. PCT/US2015/049486, dated Nov. 2015, 6 pages.
European Claims in application No. PCT/US2015/049466, dated Nov. 2015, 5 pages.
European Claims in application No. PCT/US2015/049464, dated Nov. 2015, 7 pages.
European Claims in application No. PCT/2015/049456, dated Nov. 2015, 7 pages.
European Patent Office, "Search Report" in application No. PCT/US2016/022503, dated May 2, 2016, 12 pages.
European Claims in application No. PCT/US2016/022503, dated May 2016, 7 pages.
The International Bureau of WIPO, "International Preliminary Report on Patentability", in application No. PCT/US2015/049466, dated Mar. 14, 2017, 9 pages.
The International Bureau of WIPO, "International Preliminary Report on Patentability", in application No. PCT/US2015/049464, dated Mar. 14, 2017, 8 pages.
The International Bureau of WIPO, "International Preliminary Report on Patentability", in application No. PCT/US2015/049456, dated Mar. 14, 2017, 9 pages.
The International Bureau of WIPO, "International Preliminary Report on Patentability", in application No. PCT/US2015/049486, dated Mar. 23, 2017, 7 pages.
Current Claims in application on. PCT/US2015/049456, dated Mar. 2017, 7 pages.
Current Claims in application No. PCT/US2015/049486, dated Mar. 2017, 6 pages.
Current Claims in application No. PCT/US2015/049466, dated Mar. 2017, 5 pages.
Current Claims in application No. PCT/US2015/049464, dated Mar. 2017, 7 pages.
Raf Tery et al ., "Using Bayesian Model Averaging to Calibrate Forecast Ensembles", dated May 2005 American Meteorological Society, 20 pages.
Berrocal et al., "Combining Spatial Statistical and Ensemble Information in Probabilistic Weather Forecasts", Monthly Weather Review, vol. 135, dated 2007 American Meteorological Society, 17 pages.
Clark et al., "The Schaake Shuffle: A Method for Reconstructing Space-Time Variability in Forecasted Precipitation and Temperature Fields", dated Feb. 2004, American Meteorological Society 20 pgs.
Dutton et al., "Calibration and combination of dynamical seasonal forecasts to enhance the value of predicted probabilities for managing risk", Springer-Verlag Berlin Heidelberg, dated 2013, 17 pages.
Gneiting et al, "Probabilistic Forecasting", Annual Reviews Further, The Annual Review of Statistics and Its Application is online at statistics.annualreviews.org, dated 2014, 30 pages.
Gneiting et al,., "Strictly Proper Scoring Rules, Prediction, and Estimation", 2007 Journal of the American Statistical Association, dated Mar. 2007, vol. 102, No. 477, Review Article, 20 pages.
Gneiting et al., "Assessing probabilistic forecasts of multivariate quantities, with an application to ensemble predictions of surface winds", dated Jun. 2008, 26 pages.
American Meteorological Society, "Bulletin of the American Meteorological Society", Early Online Release, dated 2013 American Meteorological Society, 47 pages.
Johnson et al., "Medium-range multimodel ensemble combination and calibration", Quarterly Journal of the Royal Meteorological Society, Published online Mar. 9, 2009 in Wiley InterScience, 18 pages.
Vrugt et al., "Ensemble Bayesian model averaging using Markov Chain Monte Carlo sampling", Springer Science+Business Media B.V. 2008, Received: Jun. 7, 2008 / Accepted: Sep. 25, 2008, 17 pages.
Schefzik et al., "Uncertainty Quantification in Complex Simulation Models Using Ensemble Copula Coupling", Statistical Science, dated 2013, vol. 28, No. 4, 25 pages.
Scheuerer et al., "Spatially adaptive post-processing of ensemble forecasts for temperature", dated Feb. 6, 2013, 17 pages.
Scheuerer, M., "Probabilistic quantitative precipitation forecasting using Ensemble Model Output Statistics", Quarterly Journal of the RoyalMeteorological Society, dated Apr. 17, 2013, 11 pages.
Sloughter et al., "Probabilistic Quantitative Precipitation Forecasting Using Bayesian Model Averaging", dated Sep. 2007 American Meteorological Society, 12 pages.
Thorarinsdottir et al., "Probabilistic forecasts of wind speed: ensemble model output statistics by using heteroscedastic censored regression", Universität Heidelberg, Germany, dated Jun. 2009, 18 pages.
Veenhuis, Bruce, "Spread Calibration of Ensemble MOS Forecasts", dated Jul. 2013, 16 pages.
Gneiting et al., "Comparing Density Forecasts Using Threshold- and Quantile-Weighted Scoring Rules", Taylor & Francis Informa Ltd, dated Aug. 19, 2015, 13 pages.
The International Bureau of WIPO, "International Preliminary Report on Patentability", in application No. PCT/US2016/022503, dated Oct. 10, 2017, 8
Current Claims in application No. PCT/US2016/022503, dated Oct. 2017, 6 pages.
Ethingon, U.S. Appl. No. 14/846,422, filed Sep. 4, 2015, Office Action, dated Feb. 2, 2018.
Ethingon, U.S. Appl. No. 14/846,661, filed Sep. 4, 2015, Office Action, dated May 17, 2018.
Ethingon, U.S. Appl. No. 14/846,659, filed Sep. 4, 2015, Office Action, dated Apr. 30, 2018.
Ethingon, U.S. Appl. No. 14/846,454, filed Sep. 4, 2015, Office Action, dated May 17, 2018.

(56) References Cited

OTHER PUBLICATIONS

Ethington, U.S. Appl. No. 14/846,454, filed Sep. 4, 2015, Office Action, dated Jun. 27, 2019.
Ethington, U.S. Appl. No. 14/846,661, filed 096/04/2015, Office Action, dated Jun. 27, 2019.
Ethington, U.S. Appl. No. 14/846,661, filed Sep. 4, 2015, Interview Summary, dated Feb. 20, 2019.
Ethington, U.S. Appl. No. 14/846,422, filed Sep. 4, 2015, Office Action, dated Jan. 30, 2019.
Ethington, U.S. Appl. No. 14/846,422, filed Sep. 4, 2015, Interview Summary, dated Mar. 7, 2019.
European Patent Office, "Search Report" in application No. 16 713 218.2-1222, dated Aug. 6, 2018, 7 pages.
European Patent Office, "Search Report" in application No. 15 775 530.7-1217, dated Sep. 13, 2018, 6 pages.
European Claims in application No. 16 713 218.2-1222, dated Aug. 2018, 7 pages.
European Claims in application No. 15 775 530.7-1217, dated Sep. 2018, 4 pages.
Ethington, U.S. Appl. No. 14/846,661, filed Sep. 4, 2015, Final Office Action, dated Dec. 4, 2018.
Ethington, U.S. Appl. No. 14/846,454, filed Sep. 4, 2015, Final Office Action, dated Jan. 2, 2019.
Current Claims in application No. 20160100949, dated Aug. 2019, 8 pages.
Buenos Aires Office Action in application No. 20160100949, dated Aug. 6, 2019, 1 page.
Ethington, U.S. Appl. No. 14/846,659, filed Sep. 4, 2015, Final Office Action, dated Oct. 5, 2018.
Australian Patent Office, "Search Report" in application No. 2016294138, dated Jan. 28, 2020, 4 pages.
Australian Claims in application No. 2016294138, dated Jan. 2020, 11 pages.
Ethington, U.S. Appl. No. 14/846,661, filed Sep. 4, 2015, Final Office Action, dated Mar. 27, 2020.
Ethington, U.S. Appl. No. 14/846,454, filed Sep. 4, 2015, Final Office Action, dated Apr. 1, 2020.
Liebig et al., "Greenhouse Gas Contributions and Mitigation Potential of Agricultural Practices in Northwestern USA and Western Canada", Soil and Tilliage Research, dated Aug. 1, 2005, pp. 25-52.
Iftkhar et al., Modeling Managed Grassland Biomass Estimation by Using Multiemporal Remote Sensing Data—A Machine Learning Approach, IEEE, dated 2016, vol. 10. No. 7, pp. 3254-3264.
Australian Patent Office, "Search Report" in application No. 2015315001, dated Mar. 24, 2020, 6 pages.
Australian Claims in application No. 2015315001, dated Mar. 2020.

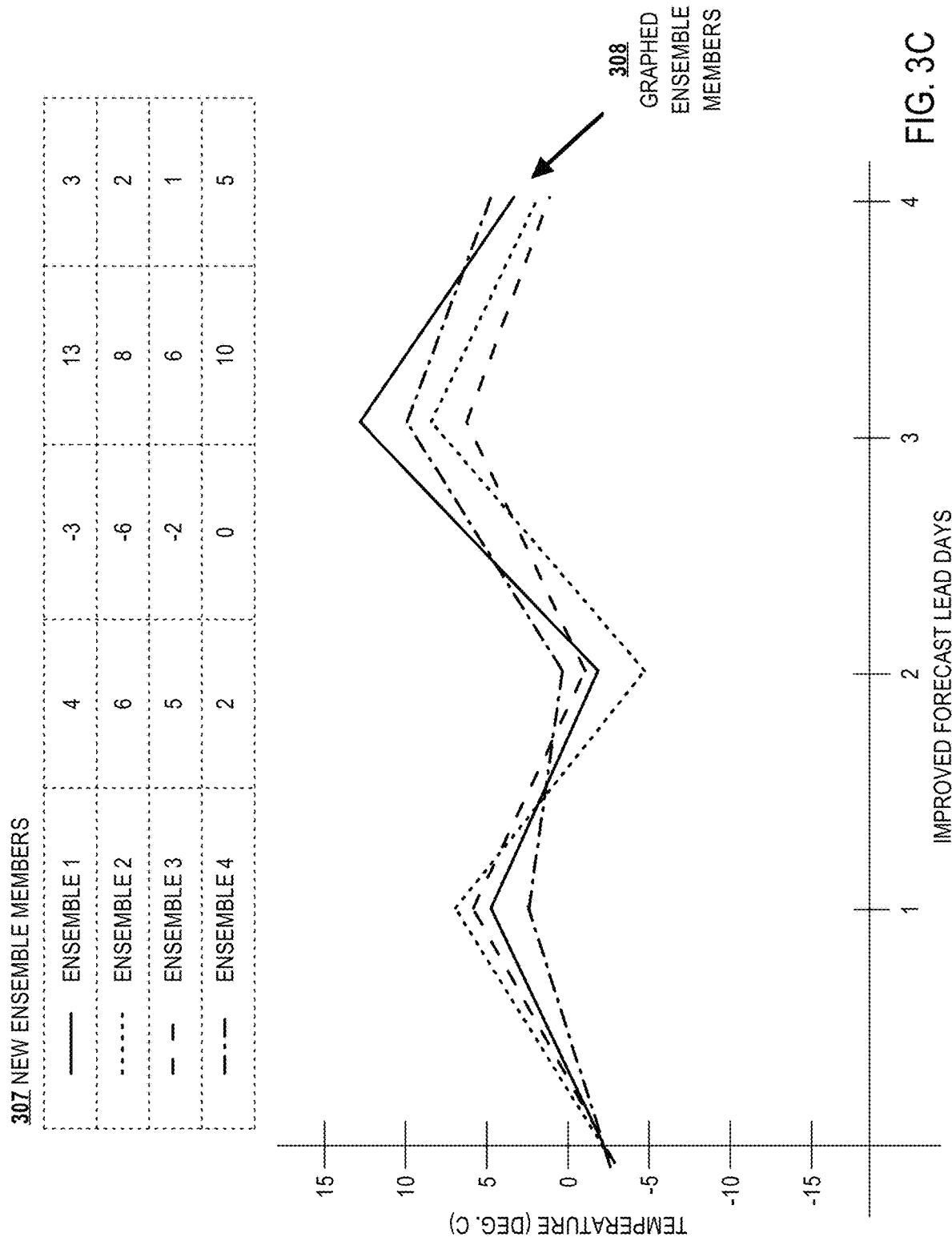

WEATHER FORECASTS THROUGH POST-PROCESSING

CROSS-REFERENCE TO RELATED APPLICATIONS

This application is related to Provisional Application 62/049,898, filed Sep. 12, 2014, entitled "Method and Systems for Managing Agricultural Activities", the entire disclosure of which is hereby incorporated by reference as if fully set forth herein.

This application is related to Provisional Application 62/049,937, filed Sep. 12, 2014, entitled "Method and Systems for Recommending Agricultural Activities", the entire disclosure of which is hereby incorporated by reference as if fully set forth herein.

This application is related to Provisional Application 62/049,909, filed Sep. 12, 2014, entitled "Method and Systems for Determining Agricultural Revenue", the entire disclosure of which is hereby incorporated by reference as if fully set forth herein.

This application is related to Provisional Application 62/049,929, filed Sep. 12, 2014, entitled "Method and Systems for Managing Crop Harvesting Activities", the entire disclosure of which is hereby incorporated by reference as if fully set forth herein.

FIELD OF THE DISCLOSURE

The present disclosure generally relates to computer systems useful in climate forecasts and agriculture. The disclosure relates more specifically to computer systems that are programmed to provide prediction data relating to temperature and precipitation, and to techniques for correcting predictions.

BACKGROUND

Weather forecasts are generally produced using a dynamic model of weather and climate evolution. Modern weather forecasts are generated using weather ensembles. A weather ensemble is a set of plausible weather forecasts based on a plurality of initial conditions and/or physical models.

Generally, weather forecasts are generated using a process known as data assimilation which makes use of measurements taken over a period of 24 hours to generate a plurality of initial conditions. Each initial condition is then used to generate plausible weather scenarios or ensemble members. The ensemble members are then combined into one weather forecast. The combination of ensemble members into a weather forecast may comprise using the average temperatures of the ensemble members, the most common temperature of the forecasts, or other modeling approaches. The ensembles are also used to determine a chance of precipitation. For example, if 20% of the ensemble members contain precipitation, a weather forecast may state that there is a 20% chance of precipitation.

Modern forecasting models suffer from a few main issues. First, the models suffer from persistent biases. Modern forecasting models make a series of approximation in order to simulate physical processes. For example, many modeling approaches use a coarse grid to approximate the spatial correlation of weather. While the approximation may be useful, the grids are often too coarse to resolve important physical processes such as convection. Second, the models tend to suffer from under-dispersion of the ensemble, often caused by an underestimation of the magnitude of systematic errors stemming from the broad approximations discussed above. Finally, modern modeling approaches only use a number of ensemble members necessary to make a probable forecast. By using a small number of ensemble members, the modern approaches fail to capture a significant fraction of potential weather outcomes. Thus, these models are inefficient at determining the risks of rare events occurring.

Another issue with modern forecasting models is that they generate weather forecasts at a generalized scale. For example, a weather forecast for a single day may include various forecasts for each city. While general forecasts are useful to a large portion of the population, farmers may require locally tailored forecasts which can predict the temperatures and likely precipitation for their individual fields. Additionally, agronomic models may require more localized temperature predictions to make accurate predictions, such as the yield of a specific crop, or good recommendations, such as the best days to harvest a crop.

SUMMARY OF THE INVENTION

The appended claims may serve as a summary of the invention.

BRIEF DESCRIPTION OF THE DRAWINGS

In the drawings:

FIG. 3C depicts an example of improved ensembles.

DETAILED DESCRIPTION

Figure 1:
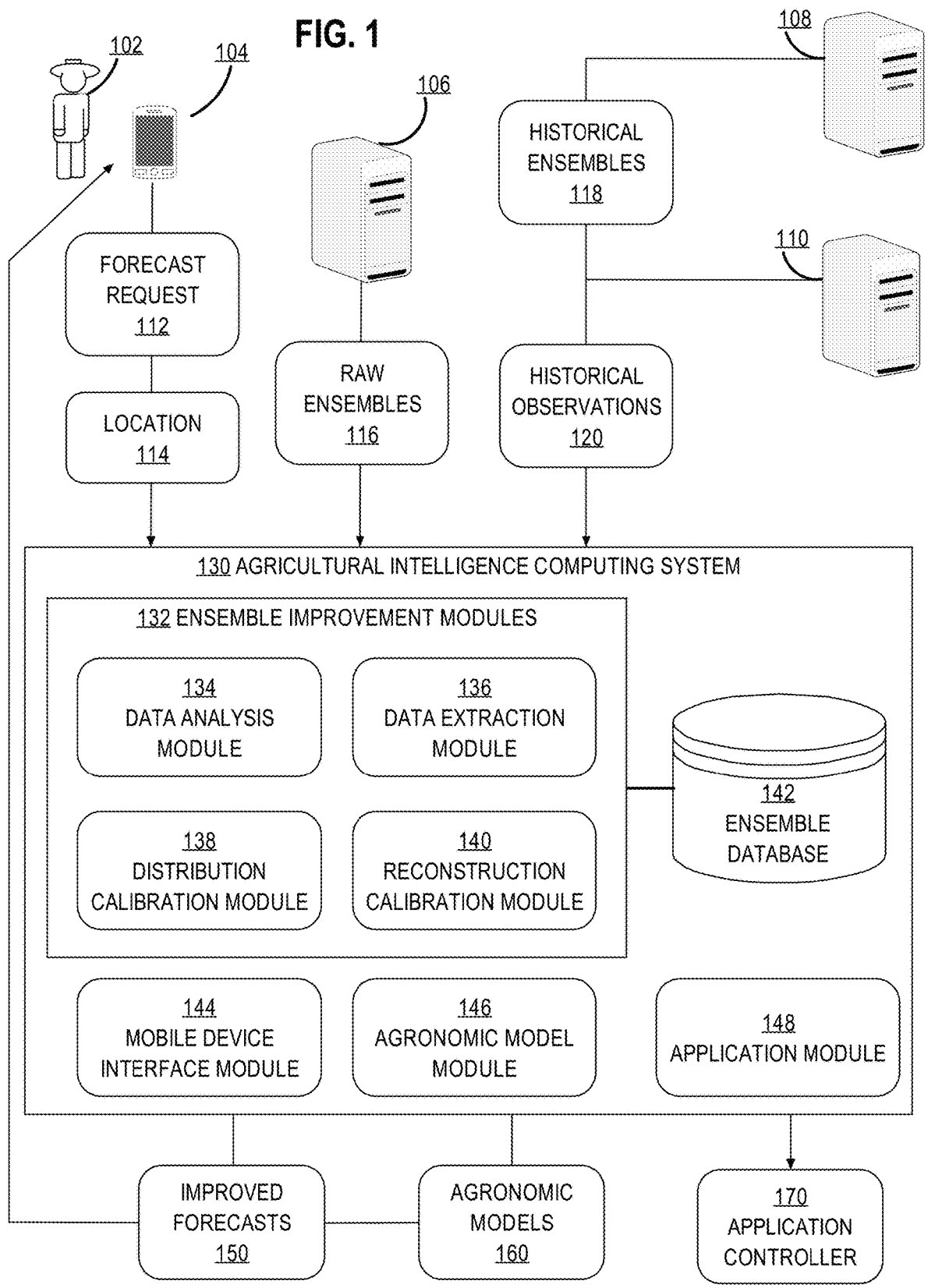
FIG. 1 is an example data flowchart of improving weather forecasts through post-processing using an agricultural intelligence computing system.

In the following description, for the purposes of explanation, numerous specific details are set forth in order to provide a thorough understanding of the present disclosure. It will be apparent, however, that the embodiments may be practiced without these specific details. In other instances, well-known structures and devices are shown in block diagram form in order to avoid unnecessarily obscuring the present disclosure. The description is provided according to the following outline:

General Overview
    Structural Overview
    Regression Fitting
    Seasonal Variation
    Application to Agronomic Models
    Analysis of Calibration Approaches
    Locational Calibration
    Historical Weather
    Selecting a Calibration Approach
    Hardware Overview
    Benefits of Certain Embodiments
    Extensions and Alternatives
    General Overview Aspects of the disclosure generally relate to computer-implemented techniques for improving weather forecasts. In an embodiment, an agricultural intelligence computing system is programmed to receive raw ensemble-based weather forecast data that is generalized at a high level, historical ensemble-based forecast data, and historical observation data that correspond to the historical ensemble-based forecast data. The agricultural intelligence computing system determines a series of historical differences between the data in the historical ensemble-based forecasts and the historical observations. When the agricultural intelligence computing system receives a request for forecasts, a data extraction module determines a series of correlations from the raw ensemble-based forecasts. The correlations and the series of historical differences are used to create probability distributions. The agricultural intelligence computing system samples the probability distributions to build new ensembles that have been corrected based on the differences and contain predictions at a more granular level.

In an embodiment, a data processing method comprises receiving over a computer network and storing in an ensemble database, a plurality of historical ensemble-based weather forecasts corresponding to one or more years of weather forecasts, each of the forecasts comprising a plurality of historical ensemble members; receiving, over the computer network, a plurality of historical weather observations and storing the plurality of historical weather observations with the plurality of historical ensemble-based weather forecasts; using a data analysis module, determining a plurality of historical difference parameters representing differences between the historical ensemble-based weather forecasts and the corresponding historical weather observations; receiving, over the computer network, a plurality of raw ensemble-based weather forecasts comprising a plurality of raw ensemble members; using a data extraction module, determining a series of correlations from the plurality of raw ensemble-based weather forecasts and storing the series of correlations in computer memory; using a distribution calibration module, creating and storing one or more distributions from the plurality of raw ensemble members, and applying the plurality of historical difference parameters to modify the one or more distributions to create one or more improved distributions; using a reconstruction calibration module, creating improved ensemble members from the one or more improved distributions and the series of correlations and creating improved ensemble-based weather forecasts from the improved ensemble members from the improved ensemble members.

Other features and aspect of the disclosure will become apparent in the drawings, description, and claims.

Structural Overview

FIG. 1 is an example data flowchart of improving weather forecasts through post-processing using an agricultural intelligence computing system.

In an embodiment, a user 102 is associated with a user device 104, which is configured to provide a forecast request 112 for a location 114 to an agricultural intelligence computing system 130. Historical forecast server 108, historical observation server 110, and current forecast server 106 are communicatively coupled to agricultural intelligence computing system 130 and are programmed or configured respectively to deliver historical ensembles 118, historical observations 120, and raw ensembles 116. Agricultural intelligence computing system 130 is programmed or configured to determine one or more weather forecasts 150 and one or more agronomic models 160 and to provide them to user device 104 of user 102.

In an embodiment, agricultural intelligence computing system 130 comprises ensemble improvement modules 132, ensemble database 142, mobile device interface module 144, agronomic model module 146, application module 148, and application controller 170. In an embodiment, ensemble improvement modules 132 include data analysis module 134, date extraction module 136, distribution calibration module 138, and reconstruction calibration module 140. In an embodiment, ensemble database 142 contains data values stored in volatile memory. Each of the foregoing elements is further described in structure and function in other sections herein. Agricultural intelligence computer system 109 also may include other devices, components or elements of a computer system such as volatile or non-volatile memory, non-volatile storage such as disk, and I/O devices as seen and described, for example, in connection with FIG. 4.

In an embodiment, ensemble improvement modules 132 are generally configured or programmed to perform translation and storage of data values, extraction of data values from a plurality of ensemble-based weather forecasts, creation and storage of distribution functions, pseudo-random selection of data values, and construction of improved weather ensembles. Data analysis module 134 is programmed or configured to determine a plurality of difference parameters representing differences between historical ensembles 118 and historical observations 120 and store the differences in ensemble database 142. Data extraction module 136 is programmed or configured to determine a series of correlations for raw ensembles 116 and store the series of correlations in ensemble database 142. Distribution calibration module 138 is programmed or configured to create and store one or more distributions for one or more lead days based on raw ensembles 116, apply the historical difference parameters to create one or more improved distributions, and store the improved distributions in ensemble database 142. Reconstruction calibration module 140 is programmed or configured to create improved ensemble members from the improved distributions and the series of correlations and combine the improved ensemble members into improved ensemble-based weather forecasts.

In an embodiment, mobile device interface module 144 is programmed or configured to receive communications from and send communications to a mobile device such as user device 104. In an embodiment, mobile device interface module 144 is further configured to interact with an application server which interacts with applications executing on a mobile device.

In an embodiment, agronomic model module 146 is programmed or configured to perform calculation and storage of agronomic factors using ensemble-based weather forecasts. Agronomic model module 146 may be configured to generate alerts based on the stored agronomic factors and send the alerts to application module 148 or user mobile device interface module 144.

In an embodiment, application module 148 is further configured to receive data from ensemble improvement modules 132, ensemble database 142, and agronomic model module 146 representing weather forecasts and agronomic models. Application module 148 may be configured to determine recommended agricultural application parameters, such as agricultural input type and agricultural input application rate, based on the weather forecasts and agronomic models.

In an embodiment, application controller 170 is configured to receive data from application module 148 representing recommended agricultural application parameters. Application controller 149 may further be configured to control an operating parameter of an agricultural vehicle or implement in order to implement the recommendation. Application controller 170 may be any of a seed meter drive, a fertilizer metering drive, a seed or fertilizer swath controller, a liquid application valve, a planting depth controller, or a planter row unit downforce controller.

Each of ensemble improvement modules 132, mobile device interface module 144, and agronomic model module 146 may be implemented using one or more computer programs or other software elements that are loaded into and executed using one or more general-purpose computers, logic implemented in field programmable gate arrays (FPGAs) or application-specific integrated circuits (ASICs).

In an embodiment, the implementation of the functions described herein for ensemble improvement modules 132, mobile device interface module 144, and agronomic model module 146 using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve as algorithms, plans, or directions that may be used to program a computer or logic to implement the functions that are described.

Agricultural intelligence computing system 130 may communicate with user device 104, historical forecast server 108, historical observation server 110, and current forecast server 106 over one or more computer networks. The network(s) may be implemented by any medium or mechanism that provides for the exchange of data between the various elements of FIG. 1. Examples include one or more Local Area Networks (LANs), Wide Area Networks (WANs), or internetworks using terrestrial, satellite or wireless links. The various elements of FIG. 1 may also have direct (wired or wireless) communications links.

In an embodiment, user 102 interacts with agricultural intelligence computing system 130 using user device 104 configured with an operating system and one or more application programs or apps. User device 104 may be a smart phone, PDA, tablet computing device, laptop computer, desktop computer or workstation, or any other computing device capable of transmitting and receiving information and performing the functions described herein. User device 104 may communicate via a network using a suitable method of interaction including a user application stored on user device 104.

The user application may provide server-side functionality, via the network to one or more user devices. In an example embodiment, user device 104 may access the user application via a web client or a programmatic client. User device 104 may transmit data to, and receive data from, one or more front-end servers. In an example embodiment, the data may take the form of requests and user information input, such as field-specific data, into the user device. In some embodiments, the user application interacts with tracking software on user device 104 which determines the location of user device 104 using standard tracking techniques such as multilateration of radio signals, the global positioning system (GPS), WiFi positioning systems, or other methods of mobile positioning.

In an embodiment, user device 104 sends forecast request 112 to agricultural intelligence computing system 130. In an embodiment, forecast request 112 is a request for a weather forecast. In other embodiments, forecast request 112 is a request for an agronomic model based on a weather forecast. User device 104 may send the request in response to input from user 102. Alternatively, user device 104 may be configured to send the requests without user interaction, such as at scheduled intervals. User device 104 also sends location 114 to agricultural intelligence computing system 130. User device 104 may determine location 114 using tracking software executing on user device 104. Alternatively, user 102 may input location 114 as coordinates corresponding to one or more fields. In an embodiment, location 114 is a precise point location, such as the exact coordinates of user device 104. In other embodiments, location 114 is a bounded area, such as a field or series of fields. Each request identified in this disclosure may be implemented using electronic digital data that is communicated between computing devices using parameterized URLs over HTTP, or another suitable communication or messaging protocol.

In an embodiment, historical forecast server 108 stores data representing historical ensembles 118 in main memory or a mass storage device. Ensembles may be stored in data structures in memory, rows in a database table, in flat files or spreadsheets, or other forms of stored digital data. Historical ensembles 118 may include a plurality of ensemble members for each day over a plurality of years. Historical ensembles 118 may comprise separate ensemble-based weather forecasts for each geographic location. Alternatively, each ensemble-based weather forecast of historical ensembles 118 may contain predictions for a plurality of locations. Historical ensembles 118 may include prediction data for the past 5 or more years. Historical ensembles 118 may also be grouped by the particular forecast in which they were used.

In an embodiment, historical observation server 110 contains historical observations 120. Historical observations 120 may include observed temperatures and precipitation values for dates corresponding to historical ensembles 118 at locations corresponding to historical ensembles 118. Precipitation values may vary from data confirming or denying the existence of precipitation to data values corresponding to a measurement of the precipitation. In an embodiment, historical observations 120 are available at a more granular level than historical ensembles 118. For example, while a historical ensemble may contain temperature predictions for an entire county, historical observations may be available for each city within the county. In an embodiment, historical observation server 110 receives historical observations 120 from a plurality of observation posts. Where observations are not available, agricultural intelligence computing system 130 may interpolate the weather values using the data from the observation posts.

In an embodiment, current forecast server 106 contains raw ensembles 116. Raw ensembles 116 may contain ensemble members grouped into corresponding weather forecasts. Raw ensembles 116 may correspond to upcoming dates at the time they are received by agricultural intelligence computing system 130. In an embodiment, raw ensembles 116 and historical ensembles 118 are sent from the same source. In alternate embodiments, raw ensembles 116 and historical ensembles 118 are created by the same source, but stored on and sent from separate servers.

Agricultural intelligence computing system 130 may receive historical ensembles 118, historical observations 120, and raw ensembles 116 and store them in ensemble database 142. As used herein, the term "database" may refer to either a body of data, a relational database management system (RDBMS), or to both. As used herein, a database may comprise any collection of data including hierarchical databases, relational databases, flat file databases, object-relational databases, object oriented databases, and any other structured collection of records or data that is stored in a computer system. Examples of RDBMS's include, but are not limited to including, Oracle® Database, MySQL, IBM® DB2, Microsoft® SQL Server, Sybase®, and PostgreSQL. However, any database may be used that enables the systems and methods described herein.

Regression Fitting

Figure 2:
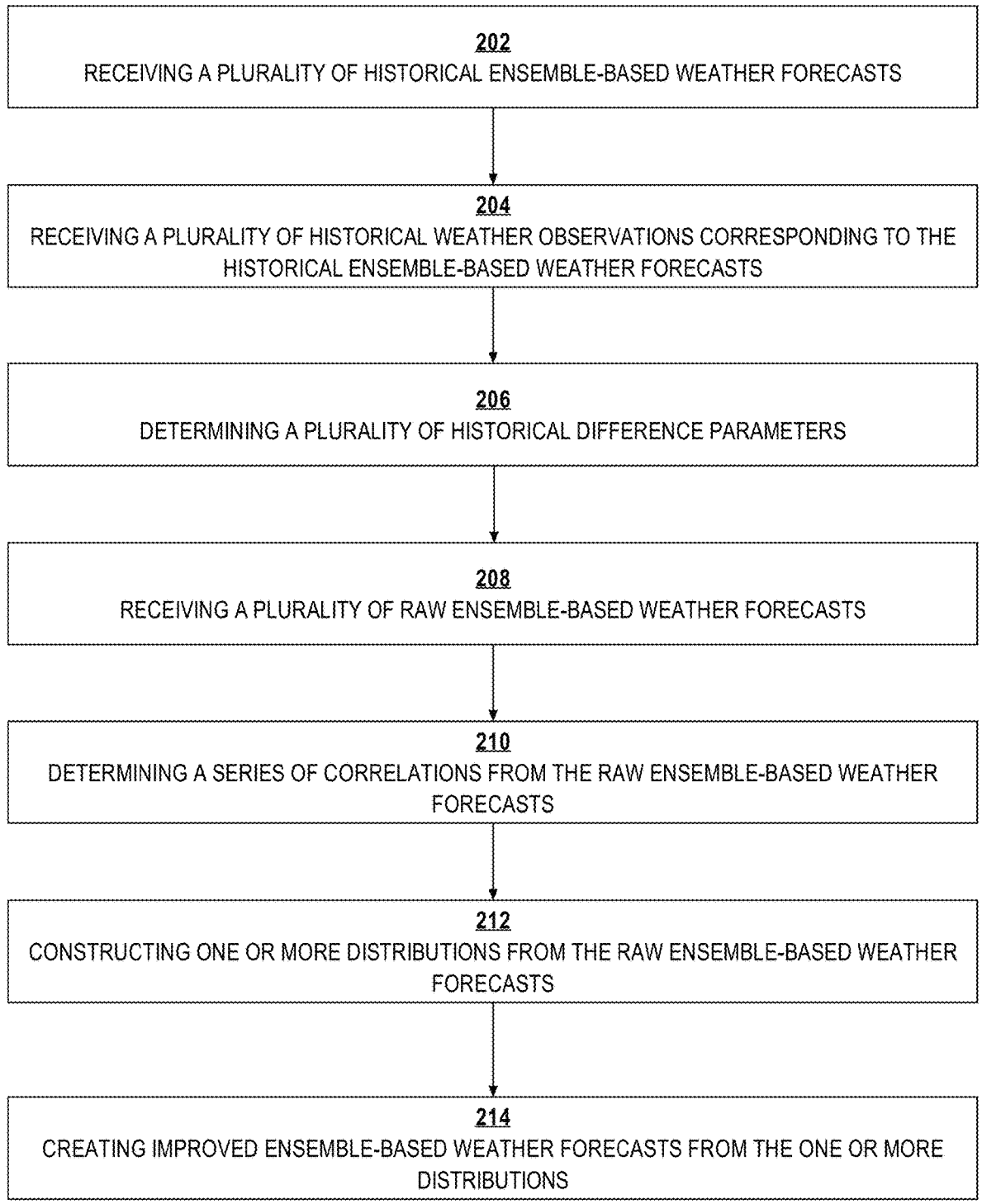
FIG. 2 depicts an example process of improving weather forecasts.

FIG. 2 depicts an example process of improving weather forecasts. For purposes of illustrating a clear example, FIG. 2 is described in the context of the system of FIG. 1, but other embodiments may be implemented using other kinds of computer systems. FIG. 2 may represent an algorithm for programming the functional elements that have been previously described with reference to FIG. 1.

At step 202, the process receives a plurality of historical ensemble-based weather forecasts. Each of the historical ensemble-based weather forecasts may contain a plurality of ensemble members. Additionally, each of the historical ensemble-based weather forecasts may contain aggregated data values from the ensemble members, such as the mean of the ensemble members for a given day, the standard deviation of the ensemble members for a given day, and the temperature prediction based on the ensemble members for a given day. In an embodiment, historical ensemble-based weather forecasts are generated for a lead time of fourteen days. The lead time is the number of days between the initial condition and the temperature prediction. Thus, each ensemble-based weather forecast may include predictions for fourteen days from the date of the prediction.

At step 204, the process receives a plurality of historical weather observations corresponding to the historical ensemble based weather forecasts. In an embodiment, the historical weather observations may originate from multiple sources. For example, one server may supply the minimum and maximum temperatures while another server may supply the precipitation values. In some examples, historical weather observations may be made by one or more stationary sensors (e.g., rain gauges, wind sensors, air temperature sensors, air moisture sensors, air pressure sensors, soil moisture sensors, soil temperature sensors) which may comprise stationary sensors located in a field or location of interest. In some examples, historical weather observations may be made by one or more on-implement sensors (e.g., air temperature sensors, air moisture sensors, air pressure sensors, soil temperature sensors, soil moisture sensors) which may comprise sensors supported by a farming vehicle or implement and disposed to engage the soil during an in-field operation (e.g., planting, tilling, fertilizing, harvesting). The stationary sensors and the on-implement sensors may be communicatively coupled to agricultural intelligence computing system 130 and may be programmed or configured respectively to deliver historical weather observations to the agricultural intelligence computing system.

At step 206, historical difference parameters are determined. For example, in the system of FIG. 1, data analysis module 134 determines a plurality of historical difference parameters. In an embodiment, historical difference parameters are model parameters which can be applied to data distributions to correct for errors or bias. Data analysis module 134 may determine the historical difference parameters for each location and each lead time at the location. The historical difference parameters for each lead time may be aggregated from the differences in that lead time for all model parameters in a year, in a season, or on a specific date over the past few years. For example, the historical difference parameters may be aggregated from all ensembles at a location with a lead time of five days from the date of prediction. Alternatively, the difference parameters may be aggregated from all ensembles at a location made in summer with a lead time of five days from the date of prediction.

At step 208, the process receives a plurality of raw ensemble-based weather forecasts. The plurality of raw ensemble-based weather forecasts may include one or more sets of raw ensembles which describe temperature and precipitation predictions at various locations.

At step 210, correlations are determined. For example, data extraction component 136 of FIG. 1 determines a series of correlations from the raw ensemble-based weather forecasts. The series of correlations may include a total mean of the raw ensembles, a total standard deviation of the raw ensembles, a mean for the raw ensembles at a specific location and lead time, and a standard deviation of the raw ensembles at a specific location and lead time.

Figure 3A:
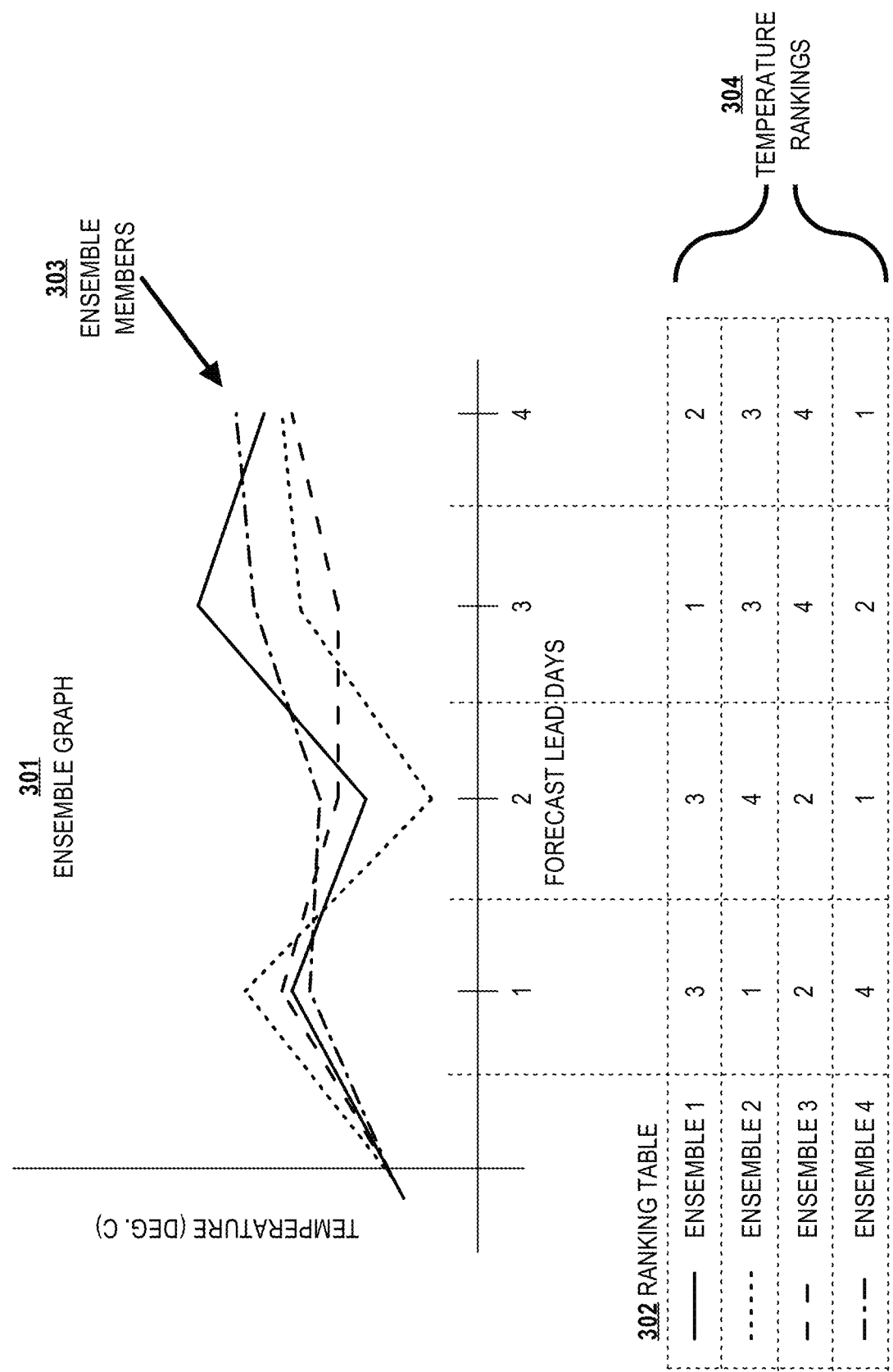
FIG. 3A depicts an example method for determining a series of correlations from raw ensemble members.

The series of correlations may also include rankings of the ensemble members at each lead day. FIG. 3A depicts an example method for determining a series of correlations from raw ensemble members. FIG. 3A contains ensemble graph 301 and ranking table 302. Ensemble graph 301 contains ensemble members 303. Each of ensemble members 303 is depicted as a series of line segments with endpoints at each of the forecast lead days. The endpoints of each line segment correspond to the estimated temperature for that specific lead day. Ranking table 302 contains temperature rankings 304 for each of ensemble members 303 at each lead day. For example, at the first lead day, ensemble 2 contained the highest temperature of ensemble members 303. Because ensemble 2 contained the highest temperature of ensemble members 303, it is given a ranking of 1. At the second lead day, ensemble 2 contained the lowest temperature of ensemble members 303 and was thus given a ranking of 4. By creating and storing rankings for the temperature values of ensemble members 303, data extraction module is able to preserve some of the spatial, temporal, and multivariate correlations of the raw ensembles.

At step 212, distributions are created and stored. For example, distribution calibration module 138 constructs one or more distributions from the raw ensemble-based weather forecasts. Constructing the distributions may comprise choosing a calibration approach for the ensemble values, choosing a distribution type, and fitting the ensemble values into the distribution based on one or more factors. One or more of the correlations determined in step 210 may be used to help construct the distributions.

Nonhomogeneous regression may be used as one calibration approach, and produces a single estimate for the probability distribution by combining all of the ensemble forecasts and using the derived quantities from the forecasts including the sample mean and sample standard deviation to create a mean and standard deviation for the distribution.

Bayesian model averaging also may be used for calibration and models the distribution by combining all of the ensemble forecasts and augmenting the terms with a function that provides the opportunity to shift the ensemble members and increase the spread of the function by increasing the uncertainty for each ensemble member. Thus, with Bayesian model averaging an offset and an added uncertainty is added to each ensemble member. This allows the system to pre-shift the distributions based on known biases and to capture additional scenarios. Distribution calibration module 138 may be programmed to implement any such approach.

In an embodiment, in the programming or configuration of distribution calibration module 138, a distribution type is pre-selected for each variable, such as temperature or precipitation. Possible distribution types include Gaussian distributions, left-censored generalized extreme value distributions, and Bernoulli-Gamma distributions.

A Gaussian distribution assumes a symmetric distribution of values around a mean value. In a Gaussian distribution, the probability of a value being below the mean value is equal to the probability that the value is above the mean value. Additionally, the spread of values is uniform such that the probability that a value is between the mean $\mu$ and $\mu+x$, where x is any number, is equal to the probability that the value is between $\mu-x$ and $\mu$.

A left censored generalized extreme value distribution is a probability distribution which features a sharp spike in probability at a low value. As the values rise past the mean value, the probabilities slowly taper off. Generalized extreme value distributions are useful to describe statistical situations that contain an upper or lower limit with a possibility of extreme events. The generalized extreme value distribution contains a heavy tail in one direction which is useful for taking into account a low probability of an extreme event, such as heavy rainfall in a storm that falls outside any historical precedent. A left censored generalized extreme value distribution is a form of the generalized extreme value distribution which contains a lower limit. Because a Gaussian distribution is symmetric, a Gaussian distribution centered on a low value would contain impossibilities, such as modeling negative rainfall. Conversely, a left censored generalized extreme value distribution may be set with a lower limit at zero to more accurately model variables such as precipitation which cannot fall below zero.

A Bernoulli-Gamma distribution is the combination of a Bernoulli distribution and a Gamma distribution. A Bernoulli distribution is a probability distribution of a random variable equaling a success at a probability, p, and failure at a probability of 1-p for a given probability, p. The Gamma distribution is a versatile distribution which can be modified to have a variety of shapes. By combining the Gamma distribution with the Bernoulli distribution, a distribution can be created that has properties similar to a Gamma distribution but with a finite probability of returning a value of zero. In an embodiment, the Gamma distribution is power transformed by exponentiating the input values to a fixed power, such as the fraction $\frac{1}{3}$, in order to better fit the distribution for modeling rainfall.

Ensemble values can be fit into the various probability distributions using a variety of techniques, including, but not limited to, maximum likelihood and continuous ranked probability score minimization. Any of these techniques may be programmed into the functional modules that have been previously described. In an embodiment, fitting the ensemble values into a probability distribution comprises creating parameters for the distribution such as the mean, standard deviation, shape, and skew based on the ensemble values.

Maximum likelihood involves selecting a set of parameters that maximizes the agreement of the distribution type with the observed data. For example, a Gaussian distribution is generally defined as containing 68% of the values within one standard deviation, 95% of the values within two standard deviations, and an equal spread of values above the mean and below the mean. Using the maximum likelihood method would involve creating estimates for the mean and standard deviation such that approximately 68% of the values of the ensembles are within one standard deviation of the mean and approximately the same number of values is above the mean as below the mean. Creating perfect estimates is not always possible depending on the input values. Thus, the maximum likelihood method fits the values of the ensembles into a distribution which would be the most likely to produce the results of the ensembles when sampled.

The continuous ranked probability score is designed to rate the quality of a forecasting model. The continuous ranked probability score is functionally a measure of the divergence of the forecast from reality. In an embodiment, a modeling method minimizes the continuous ranked probability score using the ensembles. For example, a series of Gaussian distributions may be created with varying means and standard deviations to describe a series of ensemble members. The ensemble members in this case are treated as observations. Each Gaussian distribution receives a continuous ranked probability score based on the ensemble members. The distribution which receives the lowest average score across a training dataset (where the low scores indicate a smaller distance between the distribution and the observations) is selected.

Various embodiments employ various combinations of calibration approaches, distribution types, and model fitting. For example, one approach for forecasting temperature may involve using a non-homogeneous regression model using a Gaussian distribution fit by continuous ranked probability score minimization while another approach may involve using a non-homogenous regression model using a generalized extreme value distribution fit by maximum likelihood. As another example, one approach for estimating precipitation is to use Bayesian model averaging with a Bernoulli-Gamma distribution fit by maximum likelihood while another approach is to use a non-homogenous regression with a left-censored generalized extreme value distribution fit to minimize the continuous ranked probability score.

In an embodiment, distribution calibration module 138 may improve the distributions using the historical differences. The historical differences may include differences for location, lead days, and time of year. For example, the historical differences may show that the ensembles in a specific location tend to have a right bias of 3° C. in Townsville. Distribution calibration module 138 may correct the distribution by shifting the distribution to the left by 3° C.

In some embodiments, observations that are available at more granular locations may be used to correct the more generalized ensemble-based weather forecasts. For example, the ensemble-based weather forecasts may contain a single forecast for an entire county while observations are available for different cities within the county. If City A tends to have lower temperatures than predicted and another City B tends to have higher temperatures than predicted, distribution calibration module 138 may factor these differences into the creation of the distributions for each city, such as by decreasing the prediction temperatures for City A by a value that corresponds to the average difference between temperature predictions and the actual temperatures in City A. Additionally, agricultural intelligence computing system 130 may interpolate temperatures for precise locations where observations are unavailable. Distribution calibration module 138 may use historical differences between the interpolated temperatures and the historical ensemble-based weather forecasts for each location to create improved distributions at the precise locations.

At step 214, digital data representing improved forecasts is created and stored. For example, reconstruction calibration module 140 (FIG. 1) creates improved ensemble-based weather forecasts from the one or more distributions. To create the new ensemble members, reconstruction calibration module may use pseudo-random sampling techniques to extract values from the probability distributions. The pseudo-random sampling techniques may involve randomly selecting a number from a weighted set of numbers that fit the probability distribution. For example, if a Gaussian distribution contains a mean of 10° C. and a standard deviation of 1° C., then the values between 9° C. and 11° C. would be weighted more heavily than the values below 9° C. and above 11° C.

In an embodiment, the Bayesian model averaging models may be sampled by selecting a variable from a uniform distribution between 0 and 1 to pick a specific ensemble member with a corresponding probability. In an embodiment, the probability of selecting any ensemble member is equal to the probability of selecting any other ensemble member. The distribution function is then sampled for the specific ensemble member. The process may be repeated for all ensemble members and all variables produced by a single ensemble-based forecast. Alternatively, scenario preserving techniques may be applied to Bayesian model averaging models. Scenario preserving techniques may include only selecting a single ensemble member once per weather scenario and sampling all of the variables for the single ensemble member. While the resulting samples may have the same distribution as those produced through non-scenario preserving techniques, the correlations between different variables at different locations and lead times from the initial forecast are preserved. For example, instead of independently creating samples for the maximum temperature and minimum temperature, a scenario preserving technique would sample the maximum temperature and minimum temperature for a first ensemble followed by the maximum temperature and minimum temperature for a second ensemble.

Figure 3B:
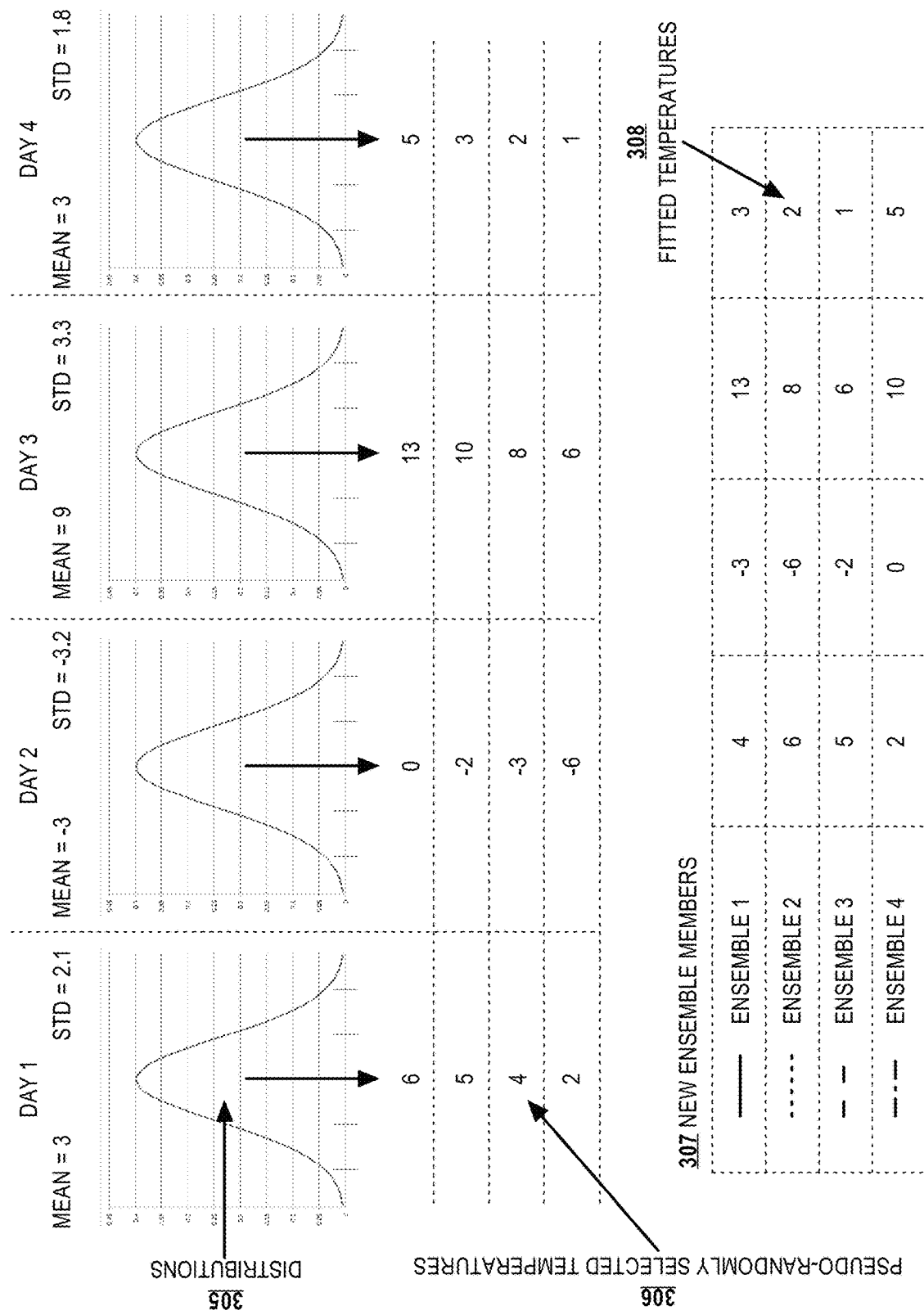
FIG. 3B depicts an example method for constructing improved ensemble members from one or more distributions.

Once temperatures have been sampled from the distributions, improved ensemble members are constructed from the sampled temperatures and one or more of the correlations determined in step 210. FIG. 3B depicts an example method for constructing improved ensemble members from one or more distributions. FIG. 3B contains distributions 305, pseudo-randomly selected temperatures 306, and new ensembles 307 and fitted temperatures 308. In the embodiment depicted in FIG. 3B, distributions 305 are Gaussian distributions. Each of distributions 305 correspond to temperature predictions for a specific lead day and contain a mean and standard deviation determined in step 212. Pseudo-randomly selected temperatures 306 are temperatures that have been sampled from distributions 305. For example, the distribution for day 1 contains a mean of 3° C. and a standard deviation of 2.1° C. The corresponding sampled temperatures, ranked from highest to lowest, are 6° C., 5° C., 4° C., and 2° C. While the sampled temperatures in FIG. 3B are depicted as integers, in various embodiments the sampled temperatures may contain any number of significant figures.

New ensemble members 307 are constructed from pseudo-randomly selected temperatures 306. Pseudo-randomly selected temperatures are used to construct fitted temperatures 308 using temperature rankings 304. For example, ensemble 2 contained the highest temperature in FIG. 3A for the first lead day. Because ensemble 2 contained the highest temperature for the first lead day in the initial ensembles, ensemble 2 in FIG. 3B is assigned a first temperature for fitted temperatures 308 of 6° C., the highest value of pseudo-randomly selected temperatures 306 for the first lead day. Because ensemble 2 contained the lowest temperature in FIG. 3A for the second lead day, ensemble 2 is assigned a second temperature for fitted temperatures 308 of −6° C., the lowest value of pseudo-randomly selected temperatures 306 for the second lead day.

FIG. 3C depicts an example of improved ensembles. New ensemble members 307 comprise values extracted from distributions 305 and fitted to the ensemble members using temperature rankings 304. Graphed ensemble members 308 are new ensemble members 307 depicted through a line graph. As with ensemble graph 301, graphed ensemble members 308 contain endpoints which correspond to a specific temperature at a specific lead day.

The method depicted in FIGS. 3A, 3B, and 3C preserves the correlations of the raw ensembles. For example, graphed ensemble members 308 contain similar line shapes to ensemble members 303 in ensemble graph 301. Additionally, unlike modern approaches, the method also allows for the creation of individual ensembles when improving weather forecasts. By preserving the actual ensembles, agricultural intelligence computing system may continually improve its method, feed the ensembles themselves into agronomic models for better estimations, and create large numbers of ensembles to determine the risks of rare events.

Seasonal Variation

In an embodiment, constructing the one or more distributions includes insertion of a seasonally dependent function. By adding terms that are seasonally dependent, agricultural intelligence computing system 130 may create more accurate calibration approaches which account for a seasonal dependence on the difference parameters. For example, if the temperature in a certain area varies more in summer than in winter, a normal distribution that takes into account the weather for the past five years would not be able to account for the increased temperature variance in summer.

In an embodiment, a normal distribution is created as a function of the mean (μ) and standard deviation (σ) as follows:

y~N (μ,σ)
$\mu = \beta_\mu^T X_\mu$
$\sigma = \beta_\sigma^T X_\sigma$ where β corresponds to the observed ensembles and X corresponds to a design matrix which includes seasonally dependent terms. The design matrices $X_\mu$ and $X\sigma$ may be defined as follows:

$$X_\mu^t = \begin{pmatrix} 1 \\ ens\_mean(t) \\ \cos(2\pi t/T) \\ \sin(2\pi t/T) \\ \cos(4\pi t/T) \\ \sin(4\pi t/T) \end{pmatrix} \text{ and } X_\sigma^t = \begin{pmatrix} 1 \\ ens\_std(t) \\ \cos(2\pi t/T) \\ \sin(2\pi t/T) \end{pmatrix}$$

where ens_mean is the mean of all of the ensembles in the raw forecasts and ens_std is the standard deviation of all of the ensembles in the raw forecasts. The cos and sin terms are harmonic terms which affect the distribution depending on the season. In the above equation, T represents 1 year and t represents a valid time for which the forecast applies. Thus, during one season, the mean and standard deviation of the distribution are affected by the historical observations, the mean of the raw ensembles, and a correction factor which exists as part of one of the harmonic terms.

A similar equation may be used to model precipitation with a seasonal dependence. In an embodiment, a left-censored generalized extreme value distribution is created as a function of the mean (μ), the standard deviation (σ), and a shape parameter (ξ) as follows:

$$y \sim LC-GEV(\mu, \sigma, \xi)$$
$$\mu = m - \sigma \frac{\Gamma(1-\xi)-1}{\xi}$$
$$m = \beta_m^T X_m$$
$$\sigma = \beta_m^T X_\sigma$$
$$\xi = -0.277 + \frac{1.277}{1+e^{-\beta_\xi}}$$

where m denotes the ensemble mean and Γ is the gamma function. β once again corresponds to the observed ensembles and X corresponds to a design matrix with seasonally dependent terms. The design matrices Xμ and Xσ may be defined as follows:

$$X_\mu^t = \begin{pmatrix} 1 \\ \text{ens\_mean}(t) \\ \text{ens\_nonzero\_frac}(t) \\ \cos(2\pi t/T) \\ \sin(2\pi t/T) \end{pmatrix} \text{ and } X_\sigma^t = \begin{pmatrix} 1 \\ \text{ens\_mean\_diff} \\ \cos(2\pi t/T) \\ \sin(2\pi t/T) \end{pmatrix}$$

where ens_nonzero_frac denotes the fraction of the raw forecasts that were nonzero and ens_mean_diff denotes the mean absolute different of the raw forecasts ensemble.

In an embodiment, the use of harmonic corrections based on seasonal dependence is made possible by incorporating two or more years of historical data into the observation matrix (β). Many methods of regression fitting with regards to forecast ensembles involve using the ensembles from the past 30 days to make corrections to current ensembles. By incorporating measurements from two or more years, agricultural intelligence computing system 130 may account for biases and errors that are dependent on seasonal variation. In functional terms, while a 30-day model may correct for ensembles of maximum temperature running high over the last 30 days or overestimation of precipitation over the last 30 days, the seasonal model may correct for ensembles of maximum temperature or precipitation running high consistently at a specific time of year over the past two or more years.

Locational Calibration

In an embodiment, the calibration techniques described herein are locally adapted to grids spread across a large area. In an embodiment, the grids are physical regions that encompass 2.5 miles by 2.5 miles of space. Calibration techniques may be executed independently for each grid. In some embodiments, agricultural intelligence computing system 130 rates the calibration techniques for each location and uses the most accurate technique for a specific location to drive the agronomic models and create predictions which are viewed by the public for the specific location. For example, agricultural intelligence computing system may use Bayesian model-averaging using a Bernoulli-Gamma distribution to predict temperatures in Springfield and non-homogeneous linear regression using a Gaussian distribution to predict temperatures in Quahog.

In an embodiment, agricultural intelligence computing system 130 receives forecast request 112 along with location 114 from user device 104. In response, agricultural intelligence computing system may create improved forecasts for one or more grids which contain location 114. Agricultural computing system 130 may then send improved forecasts 150 or agronomic models 160 to user device 104.

In some embodiments, agricultural intelligence computing system 130 may interpolate historical observations 120 for location 114. For example, if location 114 is contained by one or more grids that exist between observation posts, agricultural intelligence computing system 130 may use standard interpolation techniques to estimate observations for the grids that contain location 114. Agricultural intelligence computing system 130 may then use the interpolated observations in place of historical observations 120 when creating improved ensembles from the raw ensembles. In an embodiment, raw ensembles 116 comprise generalized ensembles that cover all locations within a specific land mass. Alternatively, if raw ensembles 116 contain gaps, ensembles may also be interpolated for areas not covered by raw ensembles 116 in a similar manner as historical observations 120.

Application to Agronomic Models

In an embodiment, agronomic model module 146 uses the improved ensembles to create agronomic models. In an embodiment, an agronomic model is a data structure in memory of agricultural intelligence computing system 130 that contains location and crop information for one or more fields. An agronomic model may also contain agronomic factors which describe conditions which may affect the growth of one or more crops on a field. Additionally, an agronomic model may contain recommendations based on agronomic factors such as crop recommendations, watering recommendations, planting recommendations, and harvesting recommendations. The agronomic factors may also be used to estimate one or more crop related results, such as agronomic yield. The agronomic yield of a crop is an estimate of quantity of the crop that is produced, or in some examples the revenue or profit obtained from the produced crop.

Heat stress describes the effect of high temperatures on the yield potential of a crop. Each crop has its own heat stress threshold which defines a maximum temperature before the yield potential of the crop is adversely affected. Additionally, crops are more adversely affected by heat stress during specific stages of development. Agronomic model module 146 may use the improved forecasts at a specific location and a crop type for the specific location to estimate the effects of both daytime and nighttime heat stress on a crop over the course of development of the crop. Agronomic model module 146 may use these estimates to create recommendations for the type of crop to plant and the ideal planting day for the crop. Additionally, agronomic model module 146 may use the estimates of the effect of heat stress on a crop to estimate the potential agronomic yield of the crop or provide estimates of the risk involved in planting the crop.

Growing degree days are a measure of heat accumulation over a day. A growing degree day is the measure of the contribution of the heat in a given day to a crop's development. A growing degree day is calculated by subtracting a base temperature from the average of the maximum temperature and minimum temperature for the day. The base temperature, which varies amongst types of crops, is the temperature below which the crop experiences no growth. Agronomic model module 146 may use the improved forecasts at a specific location to determine the growing degree days for a specific crop over the lifetime of the crop. By determining the growing degree days, agronomic model module 146 may estimate the optimal days to plant a crop, the amount of time it will take before the crop reaches development, and the optimal days to begin harvesting the crop. Agronomic model module 146 may also calculate the net gain for a specific crop based on how long the crop will take to grow at a specific location. Additionally, agronomic model module 146 may create alerts when a crop is nearing the end of its development cycle.

In an embodiment, agricultural intelligence computing system 130 uses the improved forecasts to create an agronomic model in memory or in persistent storage in response to a request from user device 104 for an agronomic model. In other embodiments, agricultural intelligence computing system 130 receives a request from a third party for an agronomic model. For example, an insurance company may request an agronomic model for an insured customer's field to determine the risks associated with the crop planted by the customer. In another example, an application server may send a request to agricultural intelligence computing system 130 to create an agronomic model for a specific user's field. Alternatively, agricultural intelligence computing system 130 may generate agronomic models periodically. Agricultural intelligence computing system 130 may also generate agronomic models in response to receiving updated weather observations or in response to creating updated improved forecasts.

Additionally, precipitation predictions may be factored into agronomic models 160 by agronomic model module 146. The amount of water a crop receives may affect the development cycle of the crop. Agronomic model module 146 may estimate the amount of water a crop needs and determine the likely amount of water the crop will receive from natural precipitation. Agronomic model module 146 may use this information to affect the estimate for agronomic yield. Additionally, agronomic model module 146 may use the precipitation predictions to generate recommendations to farmers. For example, agronomic model module 146 may recommend that a crop is not watered on a day that has a high probability of large amounts of precipitation. Alternatively, agronomic model module 146 may recommend that a crop receives extra water if the chances of precipitation are extremely low for the foreseeable future.

In an embodiment, agricultural intelligence computing system 130 sends agronomic models 160 to user device 104. In other embodiments, agricultural intelligence computing system 130 creates recommendations using agronomic models 160 and sends the recommendations to user device 104. In some embodiments, climatology computing system may generate alerts based on information in agronomic models 160. For example, agricultural intelligence computing system 130 may generate an alert to be sent to user device 102 in response to determining that a specific crop is about to reach the end of its development based on the estimated number of growing degree days since the crop was planted. Agricultural intelligence computing system 130 may also store agronomic models 160 in memory. Stored agronomic models may later be used to improve methods used by agronomic model module 146 or to rate the various modeling methods.

In an embodiment, weather forecasts 150 and agronomic models 160 are sent to application module 148. Application module 148 may use the data values of weather forecasts 150 and agronomic models 160 to create application parameters for application controller 170. For example, weather forecasts 150 may indicate a lack of upcoming precipitation and agronomic models 160 may indicate a recommended amount of water for a specific crop. Application module 148 may use the precipitation and water data for the crop to generate parameters for a liquid application valve that causes the liquid application valve to increase the amount of water released to the specific crop. Application module 148 may send the application parameters to application controller 170. Application controller 170 may then implement the application parameters, such as increasing the amount of water released to a specific crop.

Analysis of Calibration Approaches

In an embodiment, agricultural intelligence computing system 130 may receive observations that correspond to improved ensembles created by agricultural intelligence computing system 130. Agricultural intelligence computing system 130 may use the observations to rate the various modeling systems used by distribution calibration module 138 to create improved weather forecasts. Based on the ratings of the various modeling systems, agricultural intelligence computing system 130 may change modeling methods or update modeling methods.

In an embodiment, distribution calibration module 138 may initially use multiple combinations of calibration methods, distribution types, and model fitting methods to create improved ensembles. After receiving observations corresponding to the improved ensembles, agricultural intelligence computing system 130 may choose a model as a basis for weather forecasts. For example, agricultural intelligence computing system 130 may determine that Bayesian model-averaging using a Bernoulli-Gamma distribution fit by maximum likelihood has shown greater skill, or predictive accuracy, over the past month than the other calibration approaches. In response, agricultural intelligence computing system 130 may use Bayesian model-averaging using a Bernoulli-Gamma distribution fit by maximum likelihood to drive the agronomic models and to create predictions. Distribution calibration module 138 may, in an embodiment, continue to use the multiple combinations of calibration methods, distribution types, and model fitting. If one of the other calibration approaches begins showing higher skill then the chosen model, agricultural intelligence computing system 130 may switch calibration approaches to drive the agronomic models and to create predictions. In additional embodiments, distribution calibration module 138 may stop using a particular method if the method has consistently shown low skill over a predetermined period of time.

In an embodiment, the calibrated weather forecasts may be used to continually update the modeling methods for calibrating weather forecasts. For example, agricultural intelligence computing system 130 may determine that the calibrated forecasts using one method is consistently low during a specific season of the year. Agricultural intelligence computing system 130 may alter the seasonal correction term used for that method while keeping the seasonal correction term the same for the other methods. In another example, if agricultural intelligence computing system 130 determines that the recent results from one of the modeling methods contains a bias, agricultural intelligence computing system 130 may alter the methods for building a distribution to offset the mean by the observed bias.

In an embodiment, agricultural intelligence computing system 130 uses the calibrated forecasts as historical ensembles in creating new calibrated forecasts. The reuse of calibrated forecasts is made possible by preserving the ensemble members as shown in FIG. 3A, FIG. 3B, and FIG. 3C. In an embodiment, agricultural intelligence computing system 130 compares the results of improving raw ensembles using historical ensembles received from an outside source with the results of improving raw ensembles using improved using the calibrated forecasts. Agricultural intelligence computing system 130 may choose to use the method which provides the greatest skill to drive agronomic models and to create predictions.

Data Aggregation

The technique described above for creating improved ensemble members, which may be referred to herein as ensemble copula coupling, creates improved ensemble members that correspond to the initial ensemble members. Thus, if an initial ensemble contains 100 ensemble members, using ensemble copula coupling would produce 100 improved ensemble members.

In an embodiment, each distribution is used to create a larger number of ensemble members than existed in the initial ensemble. For example, if the initial ensemble-based weather forecast contained 100 ensemble members, the improved ensemble-based weather forecast may contain 10,000 ensemble members. Agricultural intelligence computing system 130 may create the additional ensemble members for each modeling method by continually sampling the same distributions. Each time agricultural intelligence computing system 130 samples the same distributions, new ensembles are created using the ranking method described above. For example, if the initial ensemble contained 100 ensemble members, the first sampling would create 100 corresponding ensembles and the second sampling would create an additional 100 corresponding ensemble members.

By creating a large number of ensemble members, agricultural intelligence computing system 130 is able to create more accurate predictions for the risk of rare events. For example, a drought is a rare event which may have a strong impact to a farmer. If a 5% risk of a drought exists for a specific time period, the risk may not be accurately reflected in 100 ensemble members. If 3 of the 100 ensembles show a drought, then the estimated risk of a drought would be calculated as 6% while if 2 of the 100 ensembles show a drought the estimated risk of a drought drops to 4%. If the true risk of a drought is 5%, it is possible that the sampled ensembles may not show a drought at all. In fact, the chances that none of the ensembles show a drought would be roughly 7%. In contrast, if 10,000 ensembles are used the chances that none of the ensembles show a drought drops to 0% (or approximately 10-114).

In an embodiment, the risks of rare events are used by agronomic model module 146 to affect the estimates created by agronomic model module 146. For example, if a chosen model estimates a 5% risk of a drought occurring, agronomic model module 146 may factor the 5% risk of a drought into the estimation of agronomic yield for the year.

Historical Weather

In an embodiment, the calibration techniques described herein may be used to correct simulations of past weather. Agronomic intelligence computing system 130 may access past weather ensembles received from an outside source or stored in ensemble database 142. Agronomic intelligence computing system 130 may then apply the same techniques discussed above to the past ensembles. In applying the calibration techniques discussed above, agronomic computing system 130 may use observations that are more recent than the past ensembles. For example, climatology computing system 130 may correct simulations of precipitation from 30 years ago using observations from the past five years.

Additionally, agronomic intelligence computing system 130 may correct simulations of past weather at precise locations. For example, a system that creates simulations of past weather may create the simulations at large scales such as 25 mile by 25 mile squares. If a hill exists in the middle of a 25 mile by 25 mile square, the system may miss the anomalies of weather for that location. In contrast, agronomic intelligence computing system 130 may be configured to apply calibration techniques at extremely localized locations. Thus, the historical observations used by agronomic intelligence computing system 130 may contain localized variations such as those caused by hills.

Agronomic intelligence computing system 130 may also use the techniques described herein to create and correct models in areas that do not have a large number of observation locations. Large scale numerical models may be useful for locations with few observation locations. These numerical models may still be corrected using the observations at the remaining locations to create better estimates for the areas that do not have observation locations close to them.

Selecting a Calibration Approach

In an embodiment agricultural intelligence computing system 130 contains calibration approach determination logic for selecting a calibration approach. The implementation of the calibration approach determination logic may be based, at least in part, on ratings given to each calibration for the accuracy of each weather variable. Agricultural intelligence computing approach may create the ratings based on observations that correspond to improved ensemble-based weather forecasts created by ensemble improvement modules 132 and stored in ensemble database 142. The accuracy ratings may include the mean absolute error of the calibration approach and the bias of the calibration approach.

In an embodiment, each calibration approach receives one or more accuracy ratings for each location. Agricultural intelligence computing system 130 may choose a calibration approach for each location based on the accuracy of the calibration approaches for that location. For any given ensemble-based weather forecast, agricultural intelligence computing system 130 may use multiple calibration approaches depending on the location. In an embodiment, agricultural intelligence computing system 130 applies the location based selection approach at granular levels such that an ensemble-based weather forecast that covers a large area may have different calibration approaches applied to different portions of it.

In an embodiment, each calibration approach receives one or more accuracy ratings for different lead times. For instance, one method may produce more accurate results for lead times of five days while another method may produce more accurate results for lead times of ten days. In an embodiment, a ten day forecast may include the results from the first method for the first five days and the results from the second method for second five days. Alternatively, a five day forecast may contain results from the first method and a ten day forecast may contain results from the second method.

In an embodiment, each calibration approach receives one or more accuracy ratings for different times of the year. Depending on the time of year, agricultural intelligence computing system 130 may use a different calibration approach based on the most accurate approach for that time of year. For example, a Gaussian distribution may more accurately predict temperatures in the fall when there is more temperature variation while a generalized extreme value distribution may more accurately predict temperatures in the summer when the temperatures are more heavily weighted higher values with a few anomalies in the lower values. In an embodiment, agricultural intelligence computing system 130 may use a Gaussian distribution during the fall and a generalized extreme value distribution in summer.

In an embodiment, each calibration approach receives one or more accuracy ratings for each variable and for each agronomic factor created by agronomic model module 146. Accuracy ratings may be applied to each calibration approach for temperature predictions and to each calibration approach for precipitation. Additionally, accuracy ratings may be applied to each calibration approach based on the accuracy of the predictions of growing degree days, heat stress, growing season length, and agronomic yield based on the calibration approach. For example, one calibration approach may be the most accurate at predicting the growing degree days for a crop, a second calibration approach may be the most accurate at predicting the agronomic yield, and a third model may be the most accurate at predicting the maximum temperatures. In an embodiment, agricultural intelligence computing system 130 may use all three calibration approaches independently to predict the growing degrees, the agronomic yield, and the maximum temperatures. In alternative embodiments, agricultural intelligence computing system 130 may determine one or more important variables and use the calibration approach that is most accurate at predicting the one or more important variables for all variables from the raw ensembles. Agricultural intelligence computing system may determine the accuracy ratings for agronomic factors by either re-estimating the agronomic factors after receiving observations of weather variables or by receiving input for one or more users that indicate a result, such as input identifying the actual agronomic yield of a crop, the actual agronomic yield of one of a plurality of crop or seed types planted in a field, or the actual agronomic yield of a crop in a field or region of a field. The received input may be entered by the user or determined based on data communicated to the agricultural intelligence computing system.

In an embodiment, each calibration approach receives one or more accuracy ratings for the ability to predict rare events when aggregated. For example, when a drought occurs agricultural intelligence computing system 130 may store that information in ensemble database 142 along with other instances of rare events. Agricultural intelligence computing system 130 may compare the occurrences of rare events with the corresponding ensembles for those time periods to determine which methods better predicted the rare event. In an embodiment, the methods are also rated based on predictions of rare events when no rare event occurred. For example, if a method consistently estimates high risks of rare events, the fact that the method is often wrong is considered along with the fact that the method contained the highest probability of a specific rare event when the specific rare event occurred.

In an embodiment, each calibration approach receives one or more accuracy ratings for a combination of two or more of the above described parameters. For example, each calibration approach may receive a rating for each location at each time of year. As another example, each calibration approach may receive a rating for each lead time, each variable, and each agronomic factor based on each variable. Agricultural intelligence computing system 130 may be configured to switch between methods depending on location, lead time, time of year, and prediction variables.

In an embodiment, agronomic model module 146 uses multiple modeling methods to create the agronomic models. For example, agronomic model module 146 may use the results of the method for predictions of maximum and minimum temperatures that has the highest accuracy rating in estimating temperature. If a different model has a higher accuracy rating in estimating the risk of rare events, agronomic model module 146 may use the other model to factor in the risk of rare events. Alternatively, agronomic model module 146 may be configured to use a single model for the risks of rare temperature related events and predictions of maximum and minimum temperatures to keep the results consistent.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 4:
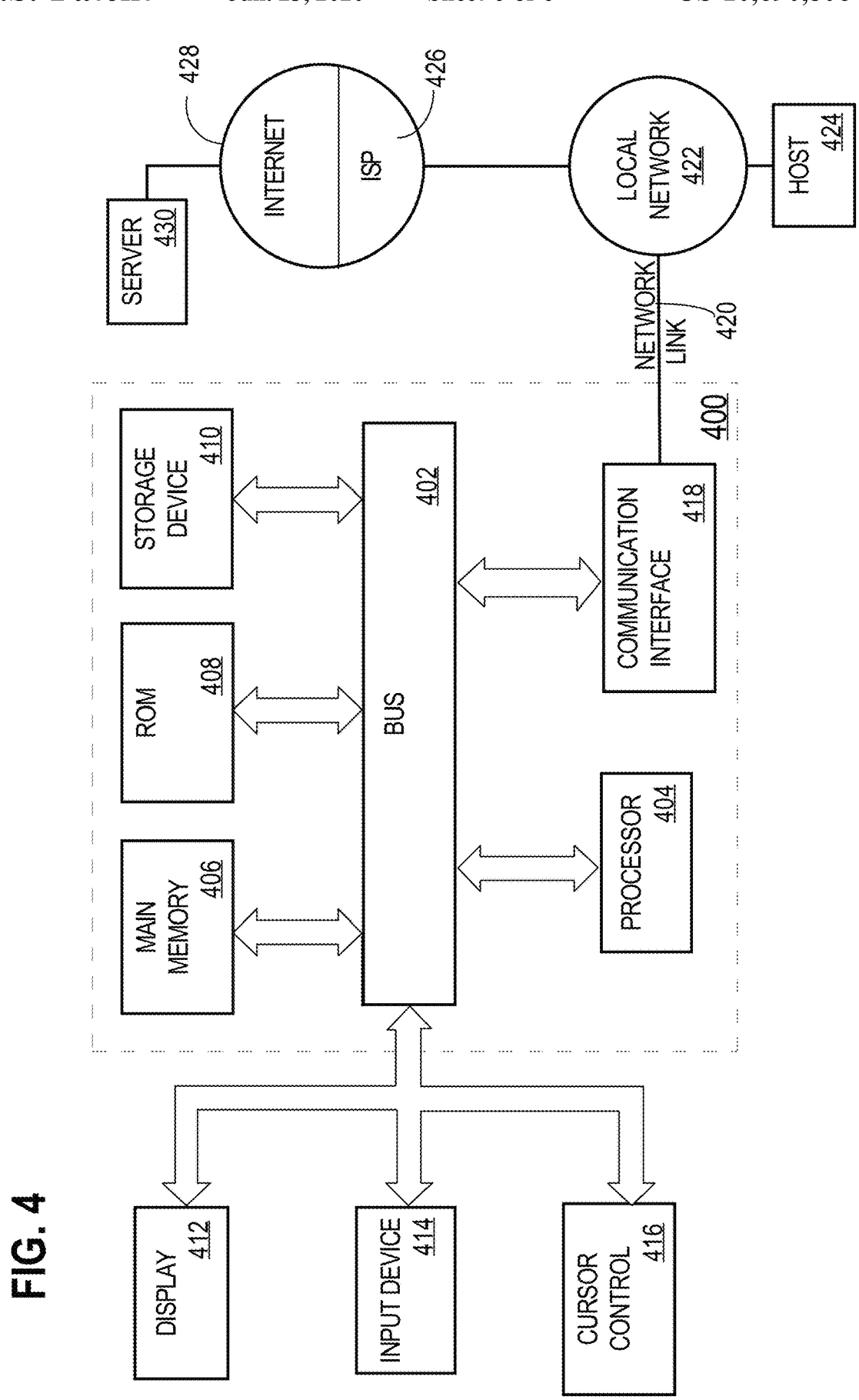
FIG. 4 is a block diagram that illustrates a computer system upon which embodiments may be implemented.

For example, FIG. 4 is a block diagram that illustrates a computer system 400 upon which embodiments may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis, such as x) and a second axis, such as y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 424. Local network 422 and Internet 424 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 424, ISP 426, local network 422 and communication interface 418.

The received code may be executed by processor 404 as it is received, and/or stored in storage device 410, or other non-volatile storage for later execution.

Benefits of Certain Embodiments

Using the techniques described herein, a computer can deliver predictions of temperature, precipitation, and other valuable weather variables that are significantly improved for accuracy and granularity. For example, the techniques herein can create more accurate predictions, increase accuracy based on seasonal dependence of weather, predict rare events, and deliver predictions at a field location level, which are otherwise not available from public and/or commercial weather data sources. The processes may be used in computer implementations to predict and deliver to a user computing device, in response to a request, precise estimates of temperature and precipitation values at growing fields or other locations even when current forecasts and observations are not available at a granular level for the areas or locations. Consequently, the performance of the end user computing device may be improved because device applications may receive and use data that otherwise would not be available, and/or avoid errors that are introduced by using data that is incomplete or contains errors.

Extensions and Alternatives

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. A method comprising:

receiving over a computer network and storing in an ensemble database, electronic digital data representing a plurality of historical ensemble-based weather forecasts corresponding to one or more years of weather forecasts, each of the forecasts comprising a plurality of historical ensemble members, wherein each of the historical ensemble members comprise a set of forecasted weather conditions for a plurality of days;

receiving, over the computer network, a plurality of historical weather observations and storing the plurality of historical weather observations with the plurality of historical ensemble-based weather forecasts;

determining a plurality of historical difference parameters representing differences between the historical ensemble-based weather forecasts and the corresponding historical weather observations;

receiving, over the computer network, a plurality of raw ensemble-based weather forecasts comprising a plurality of raw ensemble members, wherein each of the plurality of raw ensemble members comprise a set of forecasted weather conditions for a plurality of days;

determining a series of correlations from the plurality of raw ensemble-based weather forecasts and storing the series of correlations in computer memory;

creating and storing one or more distributions from the plurality of raw ensemble members, and applying the plurality of historical difference parameters to modify the one or more distributions to create one or more improved distributions;

creating improved ensemble members from the one or more improved distributions and the series of correlations and creating improved ensemble-based weather forecasts from the improved ensemble members from the improved ensemble members;

wherein the method is performed by one or more computing devices.

2. The method of claim 1 further comprising, receiving, over the network from a requesting device, one or more requests for one or more agronomic models at one or more specific locations;

generating one or more agronomic factors for the one or more specific locations using the improved ensemble-based weather forecasts and creating one or more agronomic models based at least in part on the one or more agronomic factors, the improved ensemble-based weather forecasts, and the one or more specific locations, wherein each of the agronomic models comprises crop-related information, one or more crop-related recommendations, and one or more crop related estimates.

3. The method of claim 1 wherein determining the one or more historical difference parameters comprises, creating and storing equation data representing one or more offset equations which describe the historical differences as a function of time, inserting one or more seasonal dependent terms into the equation data for the one or more offset equations, and calculating the equations based on the equation data in order to account for seasonal variations in weather.

4. The method of claim 1 wherein constructing the one or more distributions comprises:
 selecting a plurality of distribution types;
 for each of the plurality of distribution types, fitting a plurality of values relating to the plurality of the raw ensemble-based weather forecasts into a distribution type of the plurality of distribution types;
 determining one or more accuracy ratings for each of the plurality of distribution types;
 selecting one or more of the plurality of distribution types based at least on the one or more accuracy ratings.

5. The method of claim 4 wherein the plurality of values relating to the plurality of the raw ensemble-based weather forecasts includes one or more of:
 a mean of the raw ensemble-based weather forecasts;
 a standard deviation of the raw ensemble-based weather forecasts;
 a variance of the raw ensemble-based weather forecasts;
 a non-zero fraction of the raw ensemble-based weather forecasts;
 a mean absolute difference between all of the raw ensemble-based weather forecasts;
 a seasonal component corresponding to a portion of the raw ensemble-based weather forecasts;
 a time component.

6. The method of claim 4:
 wherein the one or more accuracy ratings for a particular distribution type of the plurality of distribution types is further constructed with respect to one or more additional factors, wherein the one or more additional factors comprise one or more of a location of an observation satellite, one or more forecast locations, a time of year, a lead time of the raw ensemble-based weather forecasts;
 wherein selecting the one or more of the plurality of distribution types comprises determining specific values for the one or more additional factors and selecting the distribution with the highest accuracy rating for the specific values of the one or more additional factors.

7. The method of claim 1 further comprising:
 receiving a plurality of measured weather observations corresponding to the improved ensemble-based weather forecasts;
 calculating a plurality of improved forecast differences between the improved ensemble-based forecasts and the measured weather observations;
 determining one or more improved difference parameters using the improved forecast differences;
 receiving a plurality of second raw ensemble-based weather forecasts;
 creating a plurality of second improved ensemble-based weather forecasts from the plurality of second raw ensemble-based weather forecasts and the improved difference parameters.

8. The method of claim 1 wherein the improved ensemble-based weather forecasts comprise a larger number of ensemble members than the raw ensemble-based weather forecasts, the method further comprising determining one or more risks of one or more rare events using the improved ensemble-based weather forecasts.

9. The method of claim 1 further comprising:
 receiving, over a network from a computing device, a request for an improved weather forecast for a specific location, wherein improving the raw ensemble-based weather forecasts occurs in response to the request;
 sending, over a network to the computing device, an improved weather forecast based at least in part on the improved ensemble-based weather forecast.

10. The method of claim 1 wherein creating the improved ensemble-based weather forecasts from the improved ensemble members and the series of correlations comprises:
 using pseudo-random selection logic, pseudo-randomly selecting discrete examples from the one or more distributions;
 reordering the pseudo-randomly selected discrete examples to match the ordering of the raw ensemble-based weather forecasts;
 reassembling the reordered pseudo-randomly selected discrete examples into improved ensemble members.

11. One or more non-transitory storage media storing instructions which, when executed by one or more computing devices, cause performance of:
 receiving over a computer network and storing in an ensemble database, a plurality of historical ensemble-based weather forecasts corresponding to one or more years of weather forecasts, each of the forecasts comprising a plurality of historical ensemble members, wherein each of the historical ensemble members comprise a set of forecasted weather conditions for a plurality of days;

receiving, over the computer network, a plurality of historical weather observations and storing the plurality of historical weather observations with the plurality of historical ensemble-based weather forecasts;

determining a plurality of historical difference parameters representing differences between the historical ensemble-based weather forecasts and the corresponding historical weather observations;

receiving, over the computer network, a plurality of raw ensemble-based weather forecasts comprising a plurality of raw ensemble members, wherein each of the plurality of raw ensemble members comprise a set of forecasted weather conditions for a plurality of days;

determining a series of correlations from the plurality of raw ensemble-based weather forecasts and storing the series of correlations in computer memory;

creating and storing one or more distributions from the plurality of raw ensemble members, and applying the plurality of historical difference parameters to modify the one or more distributions to create one or more improved distributions;

creating improved ensemble members from the one or more improved distributions and the series of correlations and creating improved ensemble-based weather forecasts from the improved ensemble members from the improved ensemble members.

12. The one or more non-transitory media of claim 11 wherein the instructions, when executed by the one or more computing devices, further cause performance of, receiving, over the network from a requesting device, one or more requests for one or more agronomic models at one or more specific locations;

generating one or more agronomic factors for the one or more specific locations using the improved ensemble-based weather forecasts and creating one or more agronomic models based at least in part on the one or more agronomic factors, the improved ensemble-based weather forecasts, and the one or more specific locations, wherein each of the agronomic models comprises crop-related information, one or more crop-related recommendations, and one or more crop related estimates.

13. The one or more non-transitory media of claim 11 wherein determining the one or more historical difference parameters comprises, creating and storing equation data representing one or more offset equations which describe the historical differences as a function of time, inserting one or more seasonal dependent terms into the equation data for the one or more offset equations, and calculating the equations based on the equation data in order to account for seasonal variations in weather.

14. The one or more non-transitory media of claim 11 wherein constructing the one or more distributions comprises:

selecting a plurality of distribution types;

for each of the plurality of distribution types, fitting a plurality of values relating to the plurality of the raw ensemble-based weather forecasts into a distribution type of the plurality of distribution types;

determining one or more accuracy ratings for each of the plurality of distribution types;

selecting one or more of the plurality of distribution types based at least on the one or more accuracy ratings.

15. The one or more non-transitory media of claim 14 wherein the plurality of values relating to the plurality of the raw ensemble-based weather forecasts includes one or more of:

a mean of the raw ensemble-based weather forecasts;
a standard deviation of the raw ensemble-based weather forecasts;
a variance of the raw ensemble-based weather forecasts;
a non-zero fraction of the raw ensemble-based weather forecasts;
a mean absolute difference between all of the raw ensemble-based weather forecasts;
a seasonal component corresponding to a portion of the raw ensemble-based weather forecasts;
a time component.

16. The one or more non-transitory media of claim 14:

wherein the one or more accuracy ratings for a particular distribution type of the plurality of distribution types is further constructed with respect to one or more additional factors, wherein the one or more additional factors comprise one or more of a location of an observation satellite, one or more forecast locations, a time of year, a lead time of the raw ensemble-based weather forecasts;

wherein selecting the one or more of the plurality of distribution types comprises determining specific values for the one or more additional factors and selecting the distribution with the highest accuracy rating for the specific values of the one or more additional factors.

17. The one or more non-transitory media of claim 11 wherein the instructions, when executed by the one or more computing devices, further cause performance of:

receiving a plurality of measured weather observations corresponding to the improved ensemble-based weather forecasts;

calculating a plurality of improved forecast differences between the improved ensemble-based forecasts and the measured weather observations;

determining one or more improved difference parameters using the improved forecast differences;

receiving a plurality of second raw ensemble-based weather forecasts;

creating a plurality of second improved ensemble-based weather forecasts from the plurality of second raw ensemble-based weather forecasts and the improved difference parameters.

18. The one or more non-transitory media of claim 11:

wherein the improved ensemble-based weather forecasts comprise a larger number of ensemble members than the raw ensemble-based weather forecasts, wherein the instructions the instructions, when executed by the one or more computing devices, further cause performance of determining one or more risks of one or more rare events using the improved ensemble-based weather forecasts.

19. The one or more non-transitory media of claim 11 wherein the instructions, when executed by the one or more computing devices, further cause performance of:

receiving, over a network from a computing device, a request for an improved weather forecast for a specific location, wherein improving the raw ensemble-based weather forecasts occurs in response to the request;

sending, over a network to the computing device, an improved weather forecast based at least in part on the improved ensemble-based weather forecast.

* * * * *